(12) United States Patent
Öktem et al.

(10) Patent No.: US 8,468,189 B2
(45) Date of Patent: Jun. 18, 2013

(54) ITERATED VARIATIONAL REGULARIZATION COMBINED WITH COMPONENTWISE REGULARIZATION

(75) Inventors: Ozan Öktem, Sundbyberg (SE); Hans Rullgård, Upplands Väsby (SE); Johan Lagerros, Nacka (SE); Lars-Göran Öfverstedt, Uppsala (SE); Anders Edin, Solna (SE)

(73) Assignee: Okinawa Institute of Science and Technology Promotion Corporation, Okinawa (JP)

( * ) Notice: Subject to any disclaimer, the term of this patent is extended or adjusted under 35 U.S.C. 154(b) by 944 days.

(21) Appl. No.: 12/513,943

(22) PCT Filed: Nov. 8, 2007

(86) PCT No.: PCT/EP2007/062043
§ 371 (c)(1),
(2), (4) Date: Sep. 17, 2009

(87) PCT Pub. No.: WO2008/055953
PCT Pub. Date: May 15, 2008

(65) Prior Publication Data
US 2010/0005130 A1    Jan. 7, 2010

Related U.S. Application Data

(60) Provisional application No. 60/857,478, filed on Nov. 8, 2006.

(51) Int. Cl.
*G06F 7/38* (2006.01)

(52) U.S. Cl.
USPC .......................................................... 708/446

(58) Field of Classification Search
USPC ............................................................ 708/446
See application file for complete search history.

(56) References Cited

U.S. PATENT DOCUMENTS 7,831,097 B2 * 11/2010 Chen et al. .................... 382/207
2008/0063247 A1 * 3/2008 Griswold ....................... 382/128

FOREIGN PATENT DOCUMENTS

WO         9733588         9/1997

OTHER PUBLICATIONS

Lalush D S et al: "Fast Maximum Entropy Approximation in SPECT using the RBI-MAP algorithm", IEEE Transactions on Medical Imaging, vol. 19, No. 4, Apr. 2000, pp. 286-294, XPOII035958.
Bronnikov A V: "Reconstruction of attenuation map using discrete consistency conditions", IEEE Transactions on Medical Imaging, vol. 19, No. 5, May 2000, pp. 451-462, XP011035966.

(Continued)

*Primary Examiner* — Tan V. Mai
(74) *Attorney, Agent, or Firm* — Young & Thompson

(57) ABSTRACT

The present invention relates to a solution for solving an ill-posed inverse problem in image analysis, e.g. in an electron tomography application in order to recover a structure of a sample. The solution is provided for instance as a method comprising steps of determining reliable prior knowledge about the solution, determining initial guess for the solution and determining the corresponding forward operator, deciding upon model of stochasticity, deciding on suitable regularization method, deciding on updating scheme, and producing a sequence using the set configuration.

11 Claims, 4 Drawing Sheets

OTHER PUBLICATIONS

Nuyts J et al: "Simultaneous maximum a posteriori reconstruction of attenuation and activity distributions from emission sinograms", IEEE Transactions on Medical Imaging, vol. 18, No. 5, May 1999, pp. 393-403, XP01 1035859.

De Pierro A R et al: "Fast EM-like methods for maximum a posteriori estimates in emission tomography", IEEE Transactions on Medi Cal Imaging, vol. 20, No. 4, Apr. 2001, pp. 280-288, XP0 11036077.

Hutton B F et al: "Iterative reconstruction methods", Chapter 4 in Book: Quantitative Analysis in Nuclear Medicine Imaging, Springer, 2006, pp. 107-140, XP002508074.

Oktem 0: "A short overview of the COMET (Constrained Maximum Entropy Tomography) methodology for solving inverse problems", Sidec Technologies AB, Dec. 13, 2001, XP002508075 Retrieved from t he Internet: URL:http://web.archive.org/web/20040804034.

Rullgard H et al: "COMET: Component-wise iterated relative entropy regularization", Poster, 3rd Annual Meeting of 3D-EM, Jan. 23-25, 2007, Palma De Mallorca, Spain, Jan. 2007, XP002508076, Retrieved from the Internet: URL:http://www.3dem-noe.org/research/poster014.pdf>.

"Agenda of the 3rd Annual Meeting of 3D-EM" XP002508077 Retrieved from the Internet : URL :http://www.3dem-noe .org/events/agendamajorca-2007.pdf>.

Rullgard H et al : "A componentwise iterated relative entropy regularization method with updated prior and regularization parameter ; Iterated componentwise entropy regularization", Inverse Problems, vol . 23 , No. 5, Sep. 11, 2007, pp. 2121-2139, XP020114821.

* cited by examiner (a)

(b)

(c)

(a)

(b)

(c)

ITERATED VARIATIONAL REGULARIZATION COMBINED WITH COMPONENTWISE REGULARIZATION

TECHNICAL FIELD

The present invention relates to solving ill-posed inverse problems (typically those that occur in image analysis and image enhancement) where there are several different quantities that are among the unknowns and where the error level in the data is not known beforehand. Such an inverse problem occurs in particular when one uses the transmission electron microscope in a tomographic setting (electron tomography) in order to recover the structure of the sample.

BACKGROUND OF THE INVENTION

Here we provide the background of the invention in a less formalized language, stressing ideas rather than mathematical rigour. The purpose is to provide the big picture and the mathematical formalization of all concepts introduced here is given in subsection 5.1.

A computational approach to many scientific problems is often based on mathematical models idealizing how input data is transformed into output data. In this context, a forward problem can be characterized as a problem where the goal is to determine (or predict) the outcome when the models are applied to the input data, whereas in an inverse problem the goal is to determine the causes that, using the models, yields the output data.

Most inverse problems, especially the ones that we consider, can be formulated as the problem of solving an (operator) equation. More formally, assume that the object of interest in the inverse problem can be represented, or modeled, by an elements in a suitable set $\mathcal{X}$. Assume further that one cannot directly determine $f \in \mathcal{X}$ by measurements; instead one has a model of an experiment involving f describing how input data is transformed into output data. This model, derived using information applicable to the experiment, can be represented by an operator T that maps elements in $\mathcal{X}$ into another set $\mathcal{H}$, called the data space. In reality an experiment only yields finitely many, say m, noisy data points, so $\mathcal{H}$ is in this case an m-dimensional vector space. Hence, formally we have T: $\mathcal{X} \to \mathcal{H}$ and the inverse problem can be stated as the problem of solving the equation $$T(f) = g \text{ where } g \in \mathcal{H} \text{ is given.}$$

The corresponding forward problem is to calculate g when f is given. To account for the stochasticity in the measurement process, one also needs to view data as a sample of some random variable and not as a fixed point. In this context, the inverse problem would be the problem to estimate $f \in \mathcal{X}$ from the data, which now is a single sample of some random element with values in the data space $\mathcal{H}$. A method that claims to (approximately) solve the inverse problem will be referred to as a reconstruction method.

A vast majority of inverse problems that are of interest are ill-posed. Intuitively, an inverse problem is well-posed (i.e. not ill-posed) if it has a unique solution for all (admissible) data and the solution depends continuously on the data. The last criterion simply ensures that the problem is stable, i.e. small errors in the data are not amplified. If one has non-attainable data then there are no solutions, i.e. we have non-existence. Next, there can be solutions but they are not unique, i.e. we have non-uniqueness. Finally, even if there is a unique solution, the process of inversion is not continuous, so the solution does not depend continuously on the data and we have instability. If a problem is ill-posed, non-existence is usually not the main concern. In fact, existence of a solution is an important requirement that can many times be achieved by modifying the problem as shown in subsection 5.1.2. Non-uniqueness is considered to be much more serious. The inverse problem with exact data has a unique solution whenever T is injective. In general, there is not much more to say about this case, although for a particular operator T it can of course be a difficult problem to determine if it is injective. The inverse problems occurring in practical applications, however, in general have finite data (so the data space $\mathcal{H}$ is finite dimensional), while the space $\mathcal{X}$ is infinite dimensional, and the forward operator can impossibly be injective. In this case one either has to choose one solution by some criteria or introduce uniqueness by adding additional information. This process is formalized in subsection 5.1.2. Finally, we have the case when one has instability, i.e. when the solution does not depend continuously on the data. This is the main reason for failure of many reconstruction methods that are based on numerically evaluating a discretized version of the inverse of the forward operator. Such an approach works well for well-posed problems, but if the inverse is not continuous, then one will experience numerical instabilities even when the data are only perturbed by small errors. This can partly be dealt with by the use of regularization methods which in general terms replaces an ill-posed problem by a family of neighboring well-posed problems. One has to keep in mind though that no mathematical trick can make an inherently ill-posed problem well-posed. All that a regularization method can do is to recover partial information about the solution in a stable manner. Thus, the "art" of applying regularization methods will always be to find the right compromise between accuracy and stability.

An important class of inverse problems are multicomponent inverse problems where the space $\mathcal{X}$ naturally splits into a number of components. This splitting of $\mathcal{X}$ can be used in deriving efficient reconstruction/regularization methods and regularization methods that take advantage of such a splitting is referred to here as component-wise regularization. An important example of a multicomponent inverse problem is blind deconvolution i.e. one seeks to de-convolve when the convolution kernel is unknown, so both the kernel and the function that is convolved is to be recovered. Another example is the identification problem in emission tomography where both the attenuation map and the activity map are unknown and needs to be reconstructed from measured data [8]. Finally, the inverse problem in electron tomography is an example of a multicomponent inverse problem where a number of experimental parameters must be recovered besides the scattering potential [5]. See also [7] for further examples from electrical engineering, medical and biological imaging, chemistry, robotics, vision, and environmental sciences.

Component-wise regularization/reconstruction, which is a method for dealing with multicomponent inverse problems (see subsection 5.1.6), has been described in the literature, see e.g. the survey article [7] that describes a component-wise non-linear least squares method. Iterated regularization methods have also been descried in the literature, see e.g. [12, 9, 2] for an analysis of iterated Tikhonov regularization. The combination as described here of component-wise regularization/reconstruction and iterated regularization/reconstruction is however not previously described.

SUMMARY OF THE INVENTION

It is an object of the present invention to remedy at least some of the problems with the existing technologies and provide an algorithm and method that yields a stable reconstruction of an ill-posed multicomponent inverse problem.

This invention provides a new method to combine iterated regularization with a component-wise regularization. When using a tolerance based variational regularization in any of the components, the invention provides the possibility to update the prior, which in turn redefines the regularization functional, for that component. The invention also provides a new method to iteratively update the regularization parameter for that component and this can be done without knowledge of the total error in the data. Finally, the algorithm is adaptable to a number of multicomponent inverse problem, especially to problems where the space $\mathscr{X}$ of unknowns splits into two components and the inverse problem is severely ill-posed only in one component.

The present invention is realized in a number of aspects in which a first is a method for providing a stable solution to a multicomponent inverse problem, comprising the steps of:

constructing a sequence defined as an intertwining between two sequences, the first obtained from an iterated reconstruction/regularization method and the second from a component-wise reconstruction/regularization method;
  allowing the component-wise priors to be updated within this sequence;
  allowing the component-wise regularization/reconstruction parameters to be updated within this sequence;
  in case when a tolerance based variational regularization method is used to recover a certain component, the updating of the corresponding regularization parameter (which is the tolerance level) can be made without prior knowledge of the total error in the data;

The method may further comprise the steps of:

obtaining data from an experiment for the multicomponent inverse problem;
  transferring the data to a computer;
  given a model of the probabilistic distribution, estimating the necessary parameters such as the mean and covariance matrix, of the data;
  running a computer program implementing the algorithm in claim 1;
  producing in the computer a computer readable file stored on a storage media of the solution of the multicomponent inverse problem.

A second aspect of the present invention, the prior updating within the sequence may be combined with a smoothing operation.

Yet another aspect of the present invention, a data ensemble is provided, comprising the formulation of the inverse problem, defining the forward operator modeling the experiment wherein the inverse problem and forward operator has been derived using the scientific knowledge about how input data is related to output data in the experiment, and a model of the probabilistic distribution of the data;

Yet another aspect of the present invention, a computer readable storage media containing the data ensemble may be provided.

Still another aspect of the present invention, a signal relating to the data ensemble for transportation in a communication network is provided.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION OF THE PREFERRED EMBODIMENTS

Figure 2:
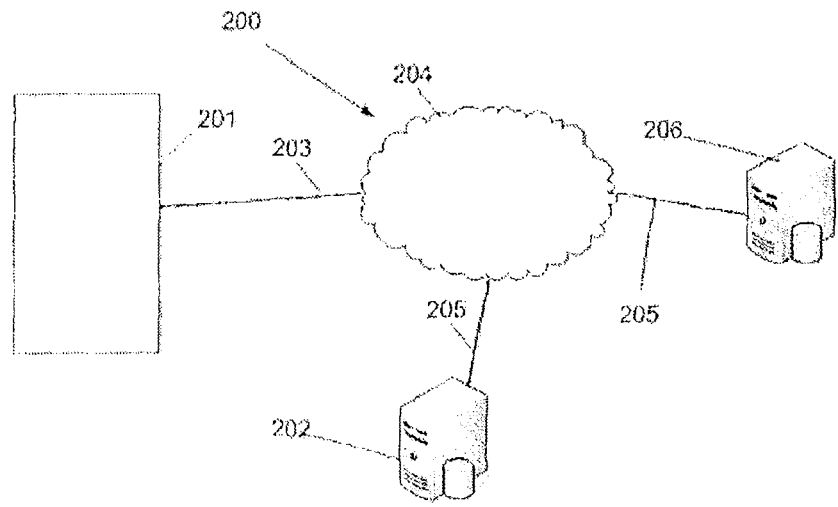
FIG. 2 illustrates schematically a system for implementing the present invention.

In FIG. 2 reference numeral 200 generally denotes a system that acquires data from an experiment that replicates the multicomponent, inverse problem in question 201 with a data acquisition device (not shown) connected 203, 205 to a processing device 202 directly or indirectly through a network 204. Data from the experiment device is transmitted to the processing device 202 that also may be arranged to control the configuration and operation of the data acquisition in the experiment 201. The data acquisition device 201 are known to the person skilled in the art in the relevant scientific discipline for the inverse problem in question and therefore not described further in this document. Data obtained in the processing device may be transmitted to other devices such as an external computer 206 connected 205 to the same network 204.

Figure 3:
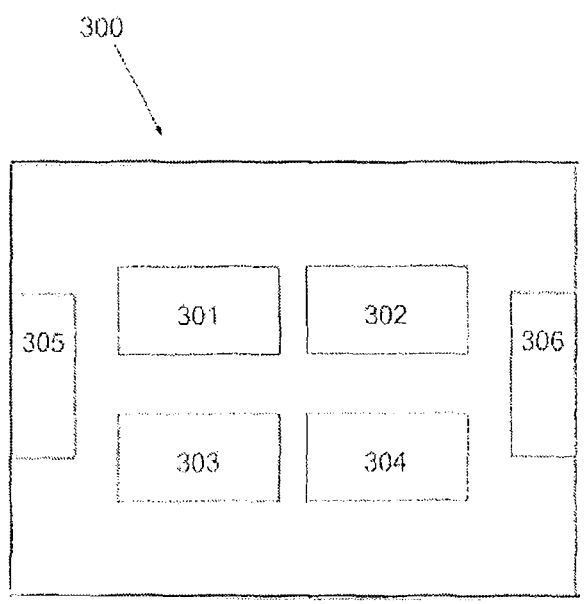
FIG. 3 illustrates schematically a device for using the present invention.

The processing device 202, 300 is shown in detail in FIG. 3, wherein a processing unit 301 handles the reconstruction procedure and interaction with the data acquisition device and user. The processing device 300 further comprises a volatile (e.g. RAM) 302 and/or non volatile memory (e.g. a hard disk or flash disk) 303, an interface unit 304. The processing device 300 may further comprise a data acquisition unit 305 and communication unit 306, each with a respective connecting interface. All units in the processing device can communicate with each other directly or indirectly through the processing unit 301. The processing unit 301 processes data, controls data acquisition, and handles interface commands using appropriate software, data and analysis results may be stored in the memory unit(s) 302, 303. The interface unit 304 interacts with interface equipment (not shown), such as input devices (e.g. keyboard and mouse) and display devices. The data acquisition unit 305 interacts with and receives data from the data acquisition device 201. The communication unit 306 communicates with other devices via for instance a network (e.g. Ethernet). Experimental data can also be stored and analyzed later in the processing device 300 or in any other suitable processing device, e.g. a server, personal computer or workstation. The analysis method according to the present invention is usually realized as computer software stored in the memory 302, 303 and run in the processing unit 301. The analysis software can be implemented as a computer program product and distributed on a removable computer readable media, e.g. diskette, CD-ROM (Compact Disk-Read Only Memory), DVD (Digital Video Disk), flash or similar removable memory media (e.g. compactflash, SD secure digital, memorystick, miniSD, MMC multimediacard, smartmedia, transflash, XD), HD-DVD (High Definition DVD), or Bluray DVD, USB (Universal Serial Bus) based removable memory media, magnetic tape media, optical storage media, magneto-optical media, bubble memory, or distributed as a propagated signal via a computer network (e.g. Internet, a Local Area Network (LAN), or similar networks). The same type of media may be used for distributing results from the measurements of the data acquisition device for post analysis at some other computational/processing device. It should be understood that the processing device may be a stand alone device or a device built into the data acquisition device. It may alternatively be a device without possibilities to control the data acquisition device and used for running image analysis, e.g. the external computer 206.

Actual experimental data may be pre-processed as to represent data originating from the multicomponent inverse problem in question. The type of pre-processing is determined by the inverse problem and the experimental setup. In a formal sense, unperturbed data are assumed to lie in the range of the forward operator. Other types of pre processing may also be done on the experimental data. The present invention is a new method to process experimental data to get better solutions of multicomponent inverse problems. This algorithm is useful for many problems, including electron microscopy tomography. The algorithm can simultaneously reconstruct several unknown components. Furthermore, the algorithm does not require an accurate estimate of the error level in the data as these can be adaptively updated within an iterative scheme.

The present invention is an algorithm and virtual machine to provide high-quality solutions (reconstructions) of data from a multicomponent inverse problem. Such data are acquired from electron microscope when used in electron tomography (ET) [5] and SPECT when there are no attenuation maps available [8].

The method applies to a large range of multicomponent inverse problems including different data acquisition geometries and stochastic models for the errors in the data. It can be adapt to each of these situations by altering the choices of the component-wise regularization/reconstruction methods and the choices for selecting and updating the corresponding priors and regularization/reconstruction parameters.

The algorithm substantially includes three steps:
1. a component-wise regularization/reconstruction combined with an iterated regularization/reconstruction,
2. iteratively component-wise updating of the regularization/reconstruction parameters,
3. iteratively component-wise updating of the prior.

The details will now be given.

Mathematical Background Information about Classical Regularization Theory

In this section we provide the mathematical background necessary for providing an in depth description of the details of the algorithm.

Inverse Problems and Concept of Ill-Posedness

We begin by formally introducing the concept of an inverse problem, the forward problem, and forward operator.

Definition 5.1.

Let $\mathcal{X}$ and $\mathcal{H}$ be Banach spaces and define data[f] as a random element in $\mathcal{H}$ whose distribution depends on $f \in \mathcal{X}$. The (measured) data, $g \in \mathcal{H}$ is defined as a sample of data[f] and the forward operator is the (not necessarily linear) mapping T: $\mathcal{X} \to \mathcal{H}$ defined by $$T(f) := E[\text{data}[f]]$$

provided that the expectation value of data[f] exists. The inverse problem is the problem to estimate $f \in \mathcal{X}$ from the data, i.e. from a single sample of data[f]. The forward problem is to generate a sample in $\mathcal{H}$ of data[f] when $f \in \mathcal{X}$ is given.

Typically, data[f] will be the sum of a random element $c_T[f]$, whose distribution depends on T(f), and an independent random element E with a fixed distribution. Another common approach is to consider the measured data g itself as an estimator of T(f), which is different from the setting in Definition 5.1 where the data g is assumed to be a sample of the random variable data[f] with expectation value T(f). The inverse problem is then reduced to the problem of solving the operator equation $$T(f) = g. \quad (1)$$

Definition 5.2.

A reconstruction method will in this paper refer to a method that claims to (approximately) solve the inverse problem in Definition 5.1 (or (1)). Formally it is defined by a reconstruction operator $R_\lambda : \mathcal{H} \to \mathcal{X}$ and the vector $\lambda \in \mathbb{R}^n$ is the parameters of the reconstruction method (it could e.g. be some stepsize or number of iterations).

We intentionally do not put additional requirements on the reconstruction operator. It is however clear that if a reconstruction method is to be of any use, the reconstruction operator should in some sense approximately provide a least squares solution of the inverse problem in question.

Definition 5.3.

We say that the data g in the inverse problem in Definition 5.1 is attainable whenever there exists $f \in \mathcal{X}$ such that T(f)=g. Moreover, we say that we have finite data if $\mathcal{H}$ is finite dimensional and otherwise we have infinite data. We have data with only additive error when $c_T(f) = T(f)$ (i.e. it is deterministic). If we in addition assume that E≡0, then we have exact data. Finally, we say that the problem is linear in f when the forward operator is a linear function of f.

The formal definition of ill- and well-posedness is due to Hadamard and it is based on the formulation in (1) of the inverse problem.

Definition 5.4.

The inverse problem in (1) is well-posed (or properly posed) if the forward operator is surjective (existence) and injective (uniqueness) when acting on $\mathcal{X}$ and the inverse of the forward operator is continuous (stability). Otherwise the problem is called ill-posed (or improperly posed).

Remark 5.5.

As stated in [3], in order to apply the above criteria for well-posedness in a specific case, one needs to specify the notion of solution, the range of T (in order to determine which data are considered admissible), and the topology that defines the concept of continuity. Mathematically, one can always make a problem well-posed by choosing specifications in an artificial way, e.g. one can artificially choose the topology in a way that makes $T^{-1}$ continuous. This is of course irrelevant in an applied problem, where the specifications have to be appropriate for the problem in question.

An important case is when the space $\mathcal{X}$ in Definition 5.1 naturally splits into a direct sum:

$$\mathcal{X} = \mathcal{V}_1 V_1 x \ldots \mathcal{V}_N. \quad (2)$$

There are two main reasons for the splitting in (2) of $\mathcal{X}$. The first is that the elements in the various components represent different physical entities. A typical example with N=2 could be that $\mathcal{V}_1 V_1$ denotes an infinite dimensional Banach space, typically some set of real valued positive functions, that represent an unknown density that is to be recovered whereas $\mathcal{V}_2 V_2$ is a finite dimensional vector space defining some experimental parameters that also needs to be recovered. The second reason is that the inverse problem might posses very different stability characteristics when one considers it as an inverse problem only in the $\mathcal{V}_j$-variable. As an example, it might, be severely ill-posed w.r.t. the elements in $\mathcal{V}_j$ for j=1, ..., N−1 and well-posed w.r.t. the elements in $\mathcal{V}_N$. We will use the term multicomponent inverse problem to refer to the inverse problem in Definition 5.1 together with the splitting (2).

As already indicated, ill-posed inverse problems require special treatment since an acceptable reconstruction method for such problems must include a regularization. Thus, in our terminology, a regularization method is a reconstruction method whereas there are reconstruction methods that are not regularization methods. In order to develop a reasonable mathematical theory for regularization methods we need of course to restrict the operators T we choose to consider. A basic assumption for a reasonable theory is to assume that $\mathscr{X}$ and $\mathscr{H}$ are Banach spaces and T: $\mathscr{X} \to \mathscr{H}$ is continuous and weakly sequentially closed [4] [3, p. 241].

Existence and Uniqueness of Solutions

Our first task is to relax the notion of a solution of the inverse problem so that existence and uniqueness is achieved in a wider class of problems.

Definition 5.6 (Least Squares Solutions).

Consider the inverse problem given in Definition 5.1 (or (1)). We say that $f^\dagger \in X$ is a least squares solution whenever $$\|\mathcal{T}(f^\dagger) - g\|_{\mathscr{H}} = \inf_{f \in \mathscr{X}} \|\mathcal{T}(f) - g\|_{\mathscr{H}}. \quad (3)$$

Since an inverse problem can have a least squares solution, even if it does not have an exact solution, this gives us the existence of solutions in a wider class of problems. Note that when data $g \in \mathscr{H}$ is attainable, then the condition in (3) reads as $T(f^\dagger) = g$. Next, we consider the problem of uniqueness. In most cases there are infinitely many solutions to (3), so we need a way to select one. Following [14], this is done by introducing a functional which performs this selection and thereby enforces uniqueness.

Definition 5.7.

Consider the inverse problem given in Definition 5.1 (or (1)) and assume that it has least squares solutions. Also, let $\rho \in \mathscr{X}$ be a fixed element which we call the prior and we are given a fixed functional $S_\rho: \mathscr{X} \to \mathbb{R}$ (that depends on the prior $\rho$). Then $f^\dagger \in \mathscr{X}$ is a $S_\rho$-minimizing least squares solution if it is a least squares solution that minimizes $S_\rho$, i.e.

$$S_\rho(f^\dagger) = \inf\{S_\rho(f); f \in \mathscr{X} \text{ fulfills (3)}\}.$$

The most common case is when $S_\rho(f) := \|f - \rho\|_{\mathscr{X}}$, , in which case one talks about $\rho$-minimum norm least squares solutions.

The functional $S_\rho$ is a measure of the distance to the prior $\rho$, even though it is not required to define a metric. The idea is that $S_\rho(f) \geq 0$ with equality when $f$ equals $\rho$. Another common requirement is that $S_\rho$ is convex. Remark 5.8. When we have a linear inverse problem, i.e. T is linear and when $S_\rho(f) = S(f-\rho)$ for some functional S, then without loss of generality one can choose $\rho \equiv 0$, since $f_0^\dagger$ is a $S_0$-minimizing least squares solution of $T(f) = g - T(\rho)$ if and only $f_0^\dagger + \rho$ is a $S_\rho$-minimizing least squares solution of $T(f) = g$.

It can happen that the equation $Tf = g$ does not have a least squares solution, but if it does it also has a $S_\rho$-minimizing least squares solution in a wide class of problems and one can prove the following theorem [15].

Theorem 5.9.

Suppose that X and H are Banach spaces, and T: $\mathscr{X} \to \mathscr{H}$. . Finally, assume that the following holds for some $\rho \in \mathscr{X}$: :
1. T is weakly closed in $\mathscr{X}$. .
2. $S_\rho$ is weakly lower semicontinuous.
3. The sets $\{f \in \mathscr{X} :S_\rho(f) \leq M\}$ are weakly-sequentially compact for all $M \in \mathbb{R}^+$. .

If the inverse problem in Definition 5.1 (or (1)) has least squares solutions, then it also has $S_\rho$-minimizing least squares solutions.

Classical Regularization Theory

Theorem 5.9 provides us with the much needed concept of a unique solution to the inverse problem in Definition 5.1 (or (1)). We are now ready to introduce the notion of a regularization method in a rigorous way and discuss what is commonly included in a mathematical analysis of such a method.

Definition 5.10 (Regularization Method).

A regularization (of the inverse problem in Definition 5.1) is defined as a family $\{R_\lambda\}_\lambda$ of continuous maps $$R_\lambda \mathscr{H} \to \mathscr{X} \text{ where } \lambda \in ]0, \lambda_0^1[\times \ldots \times ]0, \lambda_0^k[,$$

for some fixed $\lambda_0^j \in ]0, \infty]$ such that for all $g \in \mathscr{H}$ there exists a parameter choice rule $$\lambda: \mathbb{R}^+ \times \mathscr{H} \to ]0, \lambda_0^1[\times \ldots \times ]0, \lambda_0^k[$$

such that $$\limsup_{\varepsilon \to 0}\{\lambda(\varepsilon, g_\varepsilon): q_\varepsilon \in \mathscr{H}, \|g_\varepsilon - g\|_{\mathscr{H}} \leq \varepsilon\} = 0$$

$$\limsup_{\varepsilon \to 0}\{\|\mathcal{R}_{\lambda(\varepsilon, g_\varepsilon)}(g_\varepsilon) - f^\dagger\|_{\mathscr{X}}: g_\varepsilon \in \mathscr{H}, \|g_\varepsilon - g\|_{\mathscr{X}} \leq \varepsilon\} = 0$$

for some least squares solution $f^\dagger \in \mathscr{X}$. . The parameter $\lambda(\varepsilon, g_\varepsilon)$ is called the regularization parameter.

We see that each $R_\lambda$ is a reconstruction operator and the above definition formalizes the fact that a reconstruction method that is a regularization must be stable ($R_\lambda$ are continuous) and it must have a convergence property in the sense that the regularized solutions converge (in the norm) to a least squares solution of the inverse problem when the error $\epsilon$ in the data goes to zero and the regularization parameter is chosen according to the associated parameter choice rule.

Remark 5.11.

The most common case is when one has a single regularization parameter, i.e. the case $k=1$ in Definition 5.10. One can also extend the definition of a regularization given in Definition 5.10 so that it incorporates perturbations in the forward operator (modeling errors). In this case T is replaced with some approximation $T_\delta$ which is in a $\delta$-neighborhood of T in some appropriate metric. The parameter choice rule must now also include limiting as $\delta \to 0$. We refer to [1, Section 1.2] for more details on this.

In the inverse problems literature one categorizes the parameter choice rules into two distinct types, a-priori and a-posteriori parameter choice rules.

Definition 5.12.

Let $\lambda: \mathbb{R}^+ \times \mathscr{H} \to ]0, \lambda_0^1[\times \ldots \times ]0, \lambda_0^k[$ be a parameter choice rule as in Definition 5.10. If $\lambda$ does not depend on $g_\varepsilon$ but only on $\varepsilon$, then we say that $\lambda$ is an a-priori parameter choice rule. Otherwise, we say that $\lambda$ is an a-posteriori parameter choice rule.

Hence, with an a-priori parameter choice rule the choice of the regularization parameter depends only on the error level $\epsilon$ and not on the actual data $g_\varepsilon$. As shown in [3, Theorem 3.3], one cannot have a parameter choice rule that depends only on the data $g_\varepsilon$, since the resulting regularization method is either not stable or not convergent for ill-posed inverse problems.

Variational Regularization Methods

One important class of regularization methods are the variational regularization methods. Even though one can consider cases that makes use of several regularization parameters, we shall see that variational regularization methods always have a natural single regularization parameter. We therefore restrict our description to this case.

Variational regularization methods are reconstruction methods that can be formulated as solving an optimization problem which is defined by a regularization functional[1]

[1]Note that the concept of regularization operator which occurs in inverse problems literature is synonymous with the concept of regularization and is therefore not the same as regularization functional.

$$S_\rho: \mathcal{X} \to \mathbb{R}$$

and a data discrepancy functional $$D: \mathcal{H} \times \mathcal{H} \to \mathbb{R}^+.$$

Furthermore, variational regularization methods can be subdivided into tolerance and penalization based methods. The difference lies in the way the data discrepancy functional enters the optimization problem. Penalization based regularization methods are defined as $\{R_{S_\rho,\lambda}^{pen}\}_\lambda$ where $$\mathcal{R}_{S_\rho,\lambda}^{pen}(g) := \mathop{\mathrm{argmin}}_{f \in \mathcal{X}} \lambda S_\rho(f) + \mathcal{D}(\mathcal{T}(f), g) \tag{4}$$

with $\lambda$ being the regularization parameter. Tolerance based regularization methods are defined as $\{R_{S_\rho,\epsilon}^{tol}\}_\epsilon$ $$\mathcal{R}_{S_\rho,\epsilon}^{tol}(g) := \begin{cases} \mathop{\mathrm{argmin}}_{f \in \mathcal{X}} S_\rho(f) \\ \mathcal{D}(\mathcal{T}(f), g) \le \epsilon \end{cases} \tag{5}$$

with $\epsilon$ being the regularization parameter. In most of the cases D is given as the square of some norm on $\mathcal{H}$, but it can also be a log-likelihood function that depends on assumptions regarding the probabilistic distribution of data[f].

Iterated Reconstruction/Regularization Methods

Iterated reconstruction/regularization methods are based on defining a sequence $\{f_j\}_j \subset \mathcal{X}$ that is obtained by applying a reconstruction/regularization method (which depends on the iterate j) on the inverse problem. Thus, if $f_0 \in \mathcal{X}$ is given, then one forms the iterates $\{f_j\}_j \subset \mathcal{X}$ as $$f_j := R_{\lambda_j}(g; f_{j-1}) \text{ where } R_{\lambda_j}(\cdot; f_{j-1}): \mathcal{H} \to \mathcal{X}.$$

The most common case is when $R_{\lambda_j}(\cdot; f_{j-1})$ is a variational regularization method for each iterate j. In such case it is common to update the prior $\rho$ for each iterate j, typically derived from the previous iterate $f_{j-1}$, which in turn effects the regularization functional. One can also choose to let the regularization parameter depend on the iterates. In particular, for iterated penalization based regularization methods this would mean that $\lambda$ in (4) varies with j and for tolerance based regularization methods, $\epsilon$ in (5) varies with j. General mathematical results about iterated reconstruction/regularization methods are scarce but the regularizing properties of the iterated Tikhonov regularization has been studied in the literature [12, 9, 2].

Component-Wise Reconstruction/Regularization

Let us now consider the inverse problem in Definition 5.1 with the splitting in (2) of $\mathcal{X}$. One can of course regularize the inverse problem in Definition 5.1 directly without considering the structure obtained from the splitting (2). This splitting can however be useful in designing a reconstruction/regularization method. Since the various components represent different physical entities, one natural approach is to regularize independently in each $\mathcal{V}_j V_j$-component. It is however non-trivial to formally show that the resulting reconstruction method is in fact a regularization of the multicomponent inverse problem given by Definition 5.1 and the splitting (2).

Let us more formally describe how to reconstruct/regularize independently in each $\mathcal{V}_j V_j$-component. Let us begin with some notation. Elements in $\mathcal{X}$ are denoted by $f := (f_1, \ldots, f_N)$ where $f_j \in \mathcal{V}_j V_j$. For a given $l = 1, \ldots, N$ we introduce the following notation:

$$f^{/l} := (f_1, \ldots, f_{l-1}, f_{l+1}, f_N) \in \mathcal{V}_1 \times \ldots \times \mathcal{V}_{l-1} \times \mathcal{V}_{l+1} \times \ldots \times \mathcal{V}_N.$$

and $(f^{/l}; h) := (f_1, \ldots, f_{l-1}, h, f_{l+1}, f_N)$ for $h \in \mathcal{V}_l$. Now, for fixed $f^{/l}$, assume that the family $\{R_{l,\lambda}(\cdot; f^{/l})\}_\lambda$ continuous maps $$R_{l,\lambda}(\cdot; f^{/l}): \mathcal{H} \to \mathcal{V}_l.$$

defines a reconstruction (and if necessary a regularization) method of the corresponding inverse problem where the forward operator is given by $$h \to T((f^{/l}; h)) \text{ for } h \in \mathcal{V}_l.$$

We now define a sequence $\{f_j\}_j \subset \mathcal{X}$ in the following way: Assume that $f_0 \in \mathcal{X}$ is given and let $\sigma: \mathbb{N} \to \{1, \ldots, N\}$ denote an index ordering that determines the ordering of the component-wise regularizations. For $j \ge 1$ we now define $$f_{j,\sigma(j)} := R_{\sigma(j),\lambda^{\sigma(j)}}(g; f_{j-1}^{[\sigma(j)]})$$

$$f_j := (f_{j-1}^{[\sigma(j)]}; f_{j,\sigma(j)}). \tag{6}$$

Mathematical results of reconstruction methods that define a sequence $\{f_j\} j \subset \mathcal{X}$ are scarce and difficult to obtain. It is a highly non-trivial task to derive conditions for when such a reconstruction method is a regularization method, even though each of the maps $R_{l,\lambda}(\cdot; f^{/l})$ define a regularization in the $\mathcal{V}_j$-component. Important issues are the question of convergence, i.e. to determine whether the sequence converges and to what it converges. Another issue is to determine the influence of the choice of index ordering $\sigma$.

An example of a component-wise reconstruction method is separable non-linear least squares which is nicely reviewed in [7]. This method is applicable to multicomponent inverse problems where the forward operator is a linear combination of nonlinear functions in certain variables. Thus, in this case the space $\mathcal{X}$ splits into two parts (so N=2 in (2)) where the first part contains the linear variables and the second part contains the nonlinear variables. The idea behind separable nonlinear least squares is to explicitly eliminate the linear variables and then end up with a non-linear least squares problem for recovering the remaining non-linear variables. See [7] for further details.

The Algorithm

The algorithm we are about to describe is designed to solve a multicomponent inverse problem which we assume is given by Definition 5.1 (or in (1)) together with the splitting in (2) of the space $\mathcal{X}$. The algorithm yields a sequence which is obtained by intertwining two sequences, the first obtained from an iterated reconstruction/regularization method and the second from a component-wise reconstruction/regularization method. Within this sequence one can also update the component-wise priors and the component-wise regularization/reconstruction parameters. To simplify the notation, we describe the algorithm for the case when the space $\mathcal{X}$ splits into two parts (i.e. N=2 in (2)), so we assume that $$\mathcal{X} = \mathcal{V}_1 \times \mathcal{V}_2. \tag{7}$$

The extension to the general case is straightforward and simply makes appropriate use of (6).

Elements in $\mathcal{X}$ will be denoted by $(f, h) \in \mathcal{V}_1 \times \mathcal{V}_2$ and the (measured) data is denoted by $g \in \mathcal{H}$ (which is a sample of data[f, h]). Also, let D: $\mathcal{L}^1$ denote a fixed Hilbert space norm on $\mathcal{H}$. Next, consider the associated inverse problem of recovering the $\mathcal{V}_1$-component when the $\mathcal{V}_2$-component is assumed to be known. For fixed $h \in \mathcal{V}_2$ and fixed prior $\rho \in \mathcal{V}_1$ (see Definition 5.7) we therefore let the associated reconstruction/regularization method be denoted by $$R_{\rho,\lambda^1(\cdot;\rho,h)}^1(\cdot;h): \mathcal{H} \to \mathcal{V}_1$$

where $\lambda^1(\cdot;\rho,h)$ is the associated parameter selection rule (which now depends on $h \in \mathcal{V}_2$ and the prior $\rho \in \mathcal{V}_1$), i.e.

$$\lambda^1(\cdot;\rho,h): \mathbb{R}^+ \times \mathcal{H} \to ]0,\lambda_0^{1,1}[x \ldots x]0,\lambda_0^{1,k_1}[$$

for some fixed $\lambda_0^{1,j} \in ]0,\infty]$ with $j=1, \ldots, k_1$. Similarly, consider the inverse problem of recovering the $\mathcal{V}_2$-component when the $\mathcal{V}_1$-component is assumed to be known. For fixed $f \in \mathcal{V}_1$ and fixed prior $\tau \in \mathcal{V}_2$ (see Definition 5.7) we therefore let the associated reconstruction/regularization method be denoted by $$R_{\tau,\lambda^2(\cdot;\tau,f)}^2(\cdot;f): \mathcal{H} \to \mathcal{V}_2$$

where $\lambda^2(\cdot;\tau,f)$ is the associated parameter selection rule, (which now depends on $f \in \mathcal{V}_1$ and the prior $\tau \in \mathcal{V}_2$), i.e.

$$\lambda^2(\cdot;\tau,f): \mathcal{X} \to [0,\lambda_0^{2,1}[x \ldots x]0,\lambda_0^{2,k_2}]$$

for some fixed $\lambda_0^{2,j} \in ]0,\infty]$ with $j=1, \ldots, k_2$. Given a starting point $(f_0,h_0) \in \mathcal{V}_1 \times \mathcal{V}_2$. a prior $\rho \in \mathcal{V}_1$ in the case when the $\mathcal{V}_1$-prior is not updated and a prior $\tau \in \mathcal{V}_2$ in the case when the $\mathcal{V}_2$-prior is not updated, the iterates generate a sequence $\{(f_j,h_j)\}_j \subset \mathcal{X}$ defined recursively as follows:

$$\tau_j := \begin{cases} \mathcal{F}_2(h_{j-1}) & \text{if } \gamma/2\text{-prior is to be updated,} \\ \tau & \text{if } \gamma/2\text{-prior is not updated,} \end{cases} \quad (8)$$

$$\lambda_j^2 := \lambda^2(\varepsilon, g;, \tau_j, f_{j-1}) \quad (9)$$

$$h_j := \mathcal{R}_{\tau_j,\lambda_j^2}^2(g; f_{j-1}) \quad (10)$$

$$\rho_j := \begin{cases} \mathcal{F}_1(f_{j-1}) & \text{if } \gamma/1\text{-prior is to be updated,} \\ \rho & \text{if } \gamma/1\text{-prior is not updated,} \end{cases} \quad (11)$$

$$\lambda_j^1 := \lambda^1(\varepsilon, g; \rho_j, h_j) \quad (12)$$

$$f_j := \mathcal{R}_{\rho_j,\lambda_j^1}^1(g; h_j) \quad (13)$$

where $F_j: \mathcal{V}_j \to \mathcal{V}_j$ for $j=1,2$ is an operator that acts a smoothing.

Example 5.13.

A typical example is when $\mathcal{V}_1 \subset \mathcal{L}^1(\Omega, \mathbb{R})$ (for some domain $\Omega \subset \mathbb{R}^n$) denotes a fixed subset representing the feasible $\mathcal{V}_1$-components. In particular, it is assumed that all functions in $\mathcal{V}_1$ are non-negative and $\mathcal{V}_2$ can e.g. be a finite dimensional vector space representing unknown parameters that need to be recovered as well but that are not the primary interest. If the multicomponent inverse problem is not ill-posed w.r.t. the $\mathcal{V}_2$-component, then we recover that component by a simple least squares approach. In this case the reconstruction method $R_{\tau,\lambda^2(\cdot;\tau,f)}^2(\cdot;f)$ will not have any associated parameter selection rule $\lambda^2(\cdot;f,\tau)$ and it will not depend on any prior $\tau$ (so we therefore do not have any mooting operator $F_2$), so steps (8)-(9) above are ignored and the reconstruction operator in step (10) is given by $$\mathcal{R}^2(g; f) := \underset{h \in \gamma/2}{\mathrm{argmin}} \mathcal{D}(\mathcal{T}(f, h), g).$$

In the case with finite data (so $\mathcal{H} \cong \mathbb{R}^m$ for some m) one often defines the Hilbert space norm D as $$D(c,g) := \sqrt{(c-g)^t \cdot \Sigma^{-1} \cdot (c-g)} \text{ for } c,g \in \mathcal{H},$$

where we assume that the positive definite m×m-matrix $\Sigma$ is known (often it represents the covariance matrix of the stochastic variable data[f, h]). This concludes our example of how to recover the $\mathcal{V}_2$-component when the $\mathcal{V}_1$-component is assumed to be known. Let us now consider the converse, namely to recover the $\mathcal{V}_1$-component when the $\mathcal{V}_2$-component is assumed to be known. To make matters interesting, assume that the multicomponent inverse problem is ill-posed w.r.t. the $\mathcal{V}_1$-component. In our example we choose to use a tolerance based variational regularization method to recover elements in $\mathcal{V}_1$ (when the $\mathcal{V}_2$ $V_2$-component is known), so our regularization method $R_{\rho,\lambda^1(\cdot;\rho,h)}^1(\cdot;h)$ in step (13) is defined by a regularizing functional $S_\rho$(which in turn depends on a prior $\rho \in \mathcal{V}_1$) and the Hilbert space norm D in the following way:

$$\mathcal{R}_{\rho,\lambda^1(\varepsilon,g;\rho,h)}^1(g; h) := \begin{cases} \underset{f \in \gamma/1}{\mathrm{argmin}} S_\rho(f) \\ \mathcal{D}(\mathcal{T}(f, h), g) \leq \lambda^1(\varepsilon, g; \rho, h). \end{cases}$$

Common choices of $S_\rho$ when $\mathcal{V}_1 \subset \mathcal{L}^1(\Omega, \mathbb{R})$ are $$S_\rho(f) := \|L(f-\rho)\|_{\mathcal{V}_1}^2 \text{ where L is a linear operator,}$$

$$S_\rho(f) := \int_\Omega \left( f(x) \log\left(\frac{f(x)}{\rho(x)}\right) - f(x) + \rho(x) \right) dx.$$

The former assignment above yields the class of Tikhonov regularization methods, and the latter yields relative entropy regularization. To conclude our example we need to specify how steps (8) and (9) are defined. In the latter case one defines $\lambda^1(\varepsilon, g; \rho, h)$ and for fixed $0 < \delta < 1$, one possibility is to define it as $$\lambda^1(\varepsilon, g; \rho, h) := \varepsilon_{min}(g, h) + \delta(\mathcal{D}(\mathcal{T}(\rho, h), g) - \varepsilon_{min}(g, h)),$$

where $$\varepsilon_{min}(g, h) := \inf_{f \in \gamma/1} \mathcal{D}(\mathcal{T}(f, h), g).$$

Note that $\lambda^1(\varepsilon,g;\rho,h)$ does not explicitly depend on $\varepsilon$ so we do not assume any prior knowledge of the error level $\varepsilon$ in the data. Finally, the smoothing operator $F_1$ in step (8) is given as a smoothing convolution, i.e. $F_1(f) := \rho * \phi_b$ where the kernel $\phi_b \in \mathcal{V}_1 V_1$ could e.g. be a fixed low-pass filter with resolution given by the cut-off threshold $b > 0$. Under these assumptions, our iterates defined by steps (8)-(13) take the form $$h_j := \underset{h \in \gamma/2}{\mathrm{argmin}} \mathcal{D}(\mathcal{T}(f_{j-1}, h), g) \quad (14)$$

$$\rho_j := \begin{cases} \mathcal{F}_b(f_{j-1}) & \text{if prior is to be updated,} \\ \rho & \text{if prior is not updated,} \end{cases} \quad (15)$$

$$\varepsilon_j := \varepsilon_{min}(g, h_j) + \delta(\mathcal{D}(\mathcal{T}(\rho_j, h_j), g) - \varepsilon_{min}(g, h_j)) \quad (16)$$

-continued $$f_j := \begin{cases} \underset{f \in \gamma/1}{\mathrm{argmin}} S_{\rho_j}(f) \\ \mathcal{D}(\mathcal{T}(f, h_j), g) \le \varepsilon_j. \end{cases} \quad (17)$$

The parameters δ,b>0 are fixed and act as regularization parameters to the method. Setting δ=0 implies that there is no regularization while a choice of δ=1 implies that the data discrepancy is ignored and the solution will be equal to the prior. Increasing b simply means that we smooth the prior more. Roughly speaking, b is chosen so that spatial frequencies up to this threshold are expected to be reconstructed with reasonable stability without much regularization. Some details at higher frequencies can also be recovered, but require regularization to preserve stability. In implementations of the algorithm, the value of b is sometimes decreased as the number of iterations increases. When we keep the prior fixed, then the above iterates are a special case of a component-wise reconstruction method of the inverse problem in Definition 5.1 with the split (7) where we employ tolerance based entropy regularization to the $\mathcal{V}_1$-component and non-linear least squares reconstruction to the $\mathcal{V}_2$-component. However, in our method one also combines this with an iterated variational regularization scheme that provides has the option of modifying the regularization functional by updating the prior.

Flowchart of Invention

Figure 1:
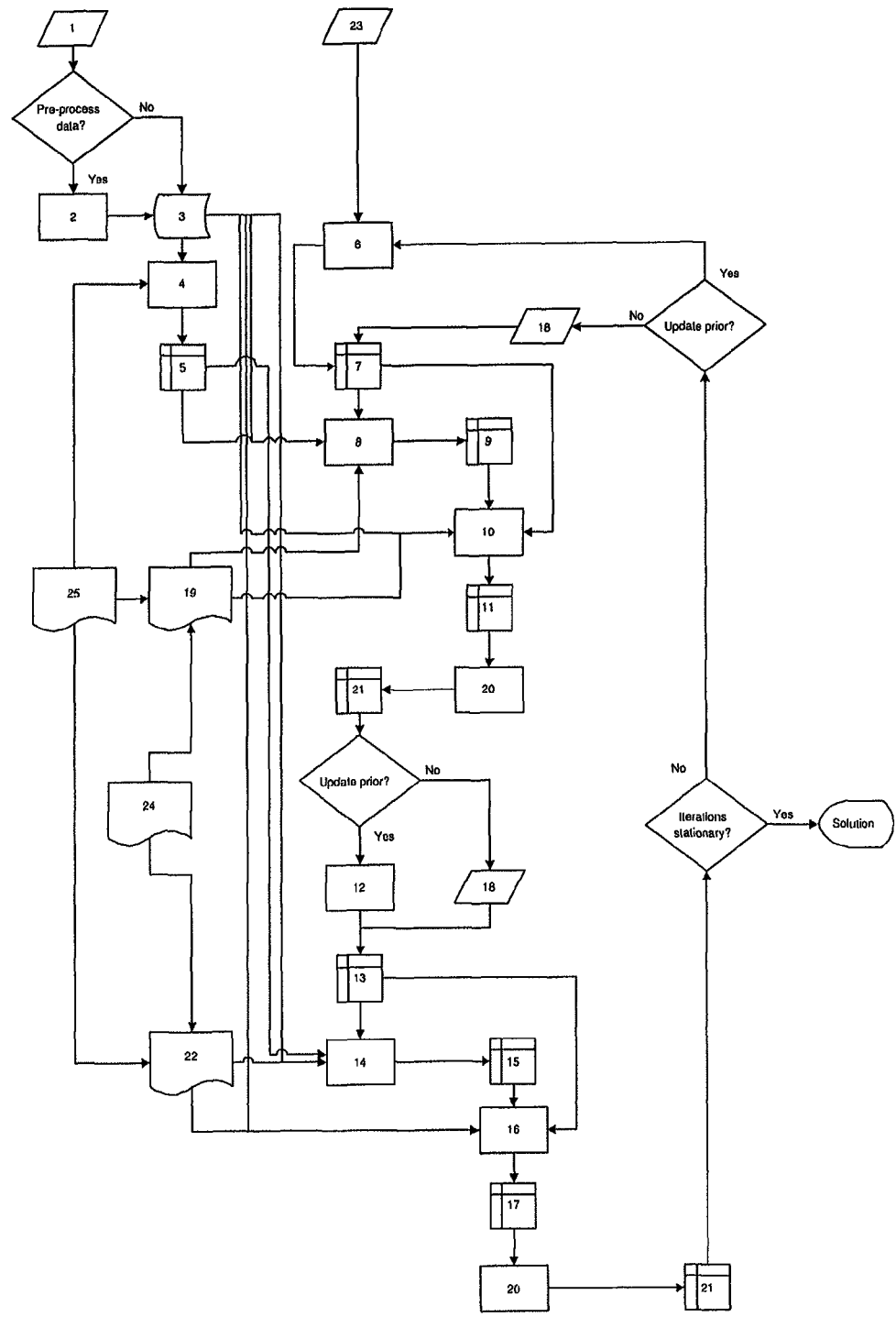
FIG. 1 illustrates schematically a general method according to the present invention.

FIG. 1 shows a flowchart of the algorithm specified in equations (8)-(13). In the figure we make use of standard flow chart symbols. The system includes an data acquisition device connected to a computer. The computer is programmed with the algorithm outlined in subsection 5.2 and it is connected to a output device, e.g. a display, a file or a printer. The result of the invention is a computer file that contains the solution to the multicomponent inverse problem. The reference numerals in FIG. 1 have the following meaning:

Reference numeral "1": The actual measured data from the experiment delivered by the data acquisition device to the computer. The concrete operation of the data acquisition device and its connection to the computer is not shown and should be understood by the persons skilled in the art for the inverse problem in question.

Reference numeral "2": The pre-processing step that transforms the measured data into a form suitable for the multicomponent inverse problem. The concrete definition of this transform should be understood by the persons skilled in the art for the inverse problem in question.

Reference numeral "3": The stored pre-processed data that acts as input data for the inverse problem.

Reference numeral "4": The process of estimating parameters necessary to specify the stochastic model for the pre-processed data. The concrete definition of this transform should be understood by the persons skilled in the art for the inverse problem in question.

Reference numeral "5": The internal representation of the stochastic model for the pre-processed data.

Reference numeral "6": The process of updating the prior for the first component.

Reference numeral "7": The internal representation of the updated prior for the first component.

Reference numeral "8": The process of updating the parameters of the re-construction/regularization method for the first component. This process depends primarily on the definition of the reconstruction/regularization method that is used and the stochastic model for the pre-processed data. It could however also depend on the updated prior and the pre-processed data itself.

Reference numeral "9": The internal representation of the updated parameters for the reconstruction/regularization method for the first component.

Reference numeral "10": The process of updating the first component by applying the associated reconstruction/regularization method with its parameters. It depends on the definition of the reconstruction/regularization method that is used and its parameters, the prior, and the pre-processed data. It could however also depend on the updated prior and the pre-processed data itself.

Reference numeral "11": The internal representation of the updated first component.

Reference numeral "12": The process of updating the prior for the second component.

Reference numeral "13": The internal representation of the updated prior for the second component.

Reference numeral "14": The process of updating the parameters of the reconstruction/regularization method for the second component. This process depends primarily on the definition of the reconstruction/regularization method that is used and the stochastic model for the pre-processed data. It could however also depend on the updated prior and the pre-processed data itself.

Reference numeral "15": The internal representation of the updated parameters for the reconstruction/regularization method for the second component.

Reference numeral "16": The process of updating the second component by applying the associated reconstruction/regularization method with its parameters. It depends on the definition of the reconstruction/regularization method that is used and its parameters, the prior, and the pre-processed data. It could however also depend on the updated prior and the pre-processed data itself.

Reference numeral "17": The internal representation of the updated second component.

Reference numeral "18": These are the initial priors.

Reference numeral "19": The document defining the reconstruction/regularization method for the first component. In most cases this depends strongly on prior knowledge of the inverse problem, the forward operator, and the stochastic model for the pre-processed data, the pre-processed data, Reference numeral "20": The intertwining operation where the previous component of the iterate in question is replaced with the updated one.

Reference numeral "21": The internal representation of the updated iterate after intertwining.

Reference numeral "22": The document, defining the reconstruction/regularization method for the second component. In most cases this depends strongly on prior knowledge of the inverse problem, the forward, operator, and the stochastic model for the pre-processed data.

Reference numeral "23": Starting point of iterative sequence.

Reference numeral "24": Document describing the forward operator.

Reference numeral "25": Document describing the stochastic model for the data.

Example of the Invention Applied to the Reconstruction Problem of Electron Tomography As we shall see, the reconstruction problem in electron tomography (ET) provides an example of a multicomponent inverse problem. We begin with a very brief recollection of the actual experimental setting in using the transmission electron microscope (TEM) in ET as means for structure determination. Next, we state the most common model for the image formation in a TEM which in turn forms the basis for the forward operator. Finally, we formally state the inverse and forward problems in ET.

The Experimental Setting

A specimen that is to be imaged in a TEM must first be physically immobilized since it is imaged in vacuum. Moreover, such specimens also need to be thin (about 100 nm) if enough electrons are to pass through to form an image. The purpose of sample preparation is to achieve this while preserving the structure of the specimen. Sample preparation techniques are rather elaborate and depend on the type of specimen, see [11] (or [6, section 2.2]) and tire references therein for more details. However, from a simplistic point of view one can say that in-vitro specimens are flash-frozen in a millisecond (cryo-EM). In-situ specimens are chemically fixed, cryo-sectioned and immuno-labeled, and can also be treated in a similar way to in-vitro specimens, [13].

Data collection in ET is done by mounting the specimen on a holder (goniometer) that allows one to change its positioning relative to the optical axis of the TEM. For a fixed position, the specimen is radiated with an electron beam and the resulting data, referred to as a micrograph, is recorded by a detector. Hence, each fixed orientation of the specimen yields one micrograph and the procedure is then repeated for a set of different positions. The most common data acquisition geometry is single axis tilting where the specimen plane is only allowed to rotate around a fixed single axis, called the tilt axis, which is orthogonal to the optical axis of the TEM. The rotation angle is called the tilt angle and the angular range is commonly in [−60°, 60°].

The Forward and Inverse Problems in ET

Before dealing with the inverse problem in ET one first needs to properly define the forward problem and the associated forward operator that models the image formation. A proper derivation of the forward operator is outside the scope of this paper and we merely provide a very brief outline on how one arrives at the expression, for the forward operator that occurs in the standard phase contrast model used by the ET community. The interested reader is referred to [5, 10] for a more detailed exposition.

The idea that data in a micrograph can be interpreted as a kind of "projection" of the specimen underlies most models for image formation used in ET. The starting point is to assume that we have perfect coherent imaging, i.e. the incoming electron wave is a monochromatic plane wave (coherent illumination) and electrons only scatter elastically. The scattering properties of the specimen are in this case given by the Coulomb potential and the electron-specimen interaction is modeled by the scalar Schrödinger equation. The picture is completed by adding a description of the effects of the optics and the detector of the TEM, both modeled as convolution operators. However, the basic assumption of perfect coherent imaging must be relaxed. Inelastic scattering introduces partial incoherence which is accounted for within a coherent framework by introducing an imaginary part to the scattering potential, called the absorption potential. The incoherence that stems from incoherent illumination is modeled by modifying the convolution kernel that describes the effect of the optics. Next, as shown in [5], taking the first order Born approximation and linearizing the intensity enables one to explicitly express the measured intensity in terms of the propagation operator acting on the scattering potential of the specimen convolved with point spread functions describing the optics and detector. The standard phase contrast model used by the ET community for the image formation in TEM is based on replacing the propagation operator by its high energy limit as the wave number tends to infinity. This yields a model for the image formation that is based on the parallel beam transform (see (20) for a definition). As we shall see, in many cases one makes one further assumption, namely that the optics and detector are perfect. The resulting model for the image formation can only account for the amplitude contrast, so the main contrast mechanism, namely phase contrast, is not adequately captured by this model for image formation.

The Scattering Potential and Intensity

In order to precisely state the forward operator we introduce the scattering potential $f: \mathbb{R}^3 \to \mathbb{C}$ that defines the structure of the specimen. Following [5], the scattering potential is given as $$f(x) := -\frac{2m}{\hbar^2}(V(x) + iV_{abs}(x)) \tag{18}$$

where m denotes the electron mass at rest, $V: \mathbb{R}^3 \to \mathbb{R}^-$ is the potential energy[2] that models elastic interaction, and $V_{abs}: \mathbb{R}^3 \to \mathbb{R}^-$ is the absorption potential that models the decrease in the flux, due to inelastic scattering, of the non-scattered and elastically scattered electrons. In scattering theory one usually wants a potential that fulfills the Rollnick condition which would be the case when $f \in \mathscr{L}^1(\Omega, \mathbb{C}) \cap L^2(\Omega, \mathbb{C})$. Under the assumptions and approximations outlined in the previous paragraph leading to the standard phase contrast model, the expression for the intensity generated by a single electron is given as

[2] The potential energy is related to the Coulomb (electrostatic) potential $U: \mathbb{R}^3 \to \mathbb{R}^+$ by V=−eU where e is the charge of the electron.

$$\mathcal{I}(f)(\omega, z) := \frac{1}{M^2}\left(1 - 2(2\pi)^{-2}\left[\left\{PSF^{re}(\omega, \cdot) \underset{\omega^\perp}{\otimes} \mathcal{P}(f^{re})(\omega, \cdot)\right\}\right.\right. \tag{19}$$
$$\left.\left.\left(\frac{z}{M}\right) + \left\{PSF^{im}(\omega, \cdot) \underset{\omega^\perp}{\otimes} \mathcal{P}(f^{im})(\omega, \cdot)\right\}\left(\frac{z}{M}\right)\right]k^{-1}\right)$$

for $\omega \tau S^2$ and $z \in \omega^\perp$ where $\omega^\perp := \{\chi \in \mathbb{R}^n : \chi \cdot w = 0\}$, k is the particle wave number[3] w.r.t. the homogeneous background medium (which in our case is vacuum), and M denotes the magnification, Moreover, the functions $f^{re}, f^{im}: \mathbb{R}^3 \to \mathbb{R}^+$ denote the real and imaginary parts of f, respectively and P denotes the parallel beam transform (X-ray transform) which is defined as

[3] We use the convention that the relation between the wave number k and the wavelength λ is given by k=2π/λ.

$$\mathcal{P}(f)(\omega, y) := \int_{t=-\infty}^{\infty} f(y + t\omega)dt \text{ for } \omega \in S^2 \text{ and } y \in \omega^\perp. \tag{20}$$

Finally, the point spread functions $PSF^{re}$ and $PSF^{im}$ in (19) model the effect of the optics and incoherent illumination of the TEM. A precise expression of these can e.g. be found in [5] or [10, chapter 65].

The Actual Measured Data and Forward Operator

The expression for the actual data measured on a micrograph needs to account for the counting stochasticity and the detector (usually a slow-scan CCD camera). Following [5], the actual data on a micrograph delivered by the detector from pixel (i,j) is given as a sample of the random variable data[f]$(\omega)_{i,j}$ which is defined as $$\text{data}[f](\omega)_{i,j} := \text{gain}_{i,j} \int_{\Delta_{i,j}} \{PSF_{det} \underset{\omega^\perp}{\circledast} c[f]_\omega\}(z)\,dz + E_{i,j} \quad (21)$$

where
1. $PSF_{det}$ is the detector point spread function, $\text{gain}_{i,j}$ is the detector gain, and $\Delta_{i,j} \subset \omega^\perp$ is the set defining the (i,j):th pixel.
2. $c[f]_\omega$ is a measure whose action on a subset $\Delta \subset \omega^\perp$ is a Poisson distributed stochastic variable with expected value $$\text{Dose}(\omega) \int_\Delta I(f)(\omega, z)\,dz$$

where $\text{Dose}(\omega)$ is the incoming dose (in number of electrons hitting the specimen per area unit).

3. $E_{i,j}$ is a stochastic variable representing the noise introduced by the detector.

We are now ready to define the forward operator and the corresponding forward/inverse problem in ET.

Definition 5.14.

The forward operator in ET, denoted by T, is defined as the expected value of $\text{data}[f](\omega)_{i,j}$, i.e.

$$T(f)(\omega)_{i,j} := E[\text{data}[f](\omega)_{i,j}] \text{ for } \omega \in S^2 \text{ and pixel } (i,j).$$

From the definition of the forward operator, it is easy to see that $$T(f)(\omega)_{i,j} = \text{gain}_{i,j} \text{Dose}(\omega) \int_{\Delta_{i,j}} \{PSF_{det} \underset{\omega^\perp}{\circledast} I(f)(\omega, \cdot)\}(z)\,dz + \varepsilon_{i,j}$$

where $\varepsilon_{i,j} := E[E_{i,j}]$. In many cases it is customary to further simplify the above expression by the following approximation:

$$\int_{\Delta_{i,j}} \{PSF_{det} \underset{\omega^\perp}{\circledast} I(f)(\omega, \cdot)\}(z)\,dz \approx |\Delta_{i,j}|\{PSF_{det} \underset{\omega^\perp}{\circledast} I(f)(\omega, \cdot)\}(z_{i,j})$$

where $|\Delta_{i,j}|$ is the area of (i, j):th pixel $\Delta_{i,j}$ and $z_{i,j} \in \Delta_{i,j}$ is some suitably chosen point (typically the midpoint). Then, the resulting expression for the forward operator reads as $$T(f)(\omega)_{i,j} = \text{gain}_{i,j}|\Delta_{i,j}|\text{Dose}(\omega)\{PSF_{det} \underset{\omega^\perp}{\circledast} I(f)(\omega, \cdot)\}(z_{i,j}) + \varepsilon_{i,j}. \quad (22)$$

Definition 5.15.

We have a fixed finite set $S_0$ of directions on a smooth curve $S \subset S^2$ that defines our data collection geometry. The scattering properties of the specimen are assumed to be fully described by the complex valued scattering potential f defined in (18). For each direction $\omega \in S_0$, the specimen is probed by a monochromatic wave and the resulting intensity is measured in a finite set of pixels (i,j) defined by fixed subsets $\Delta_{i,j} \subset \omega^\perp$. The forward problem is to generate a sample of $\text{data}[f](\omega)_{i,j}$ for $\omega \in S_0$ and the pixels (i,j) when f is given. The inverse problem is to determine f when a sample of $\text{data}[f](\omega)_{i,j}$ is known for $\omega \in S_0$ and finitely many pixels (i, j).

Additional Difficulties

The real experimental situation in ET is unfortunately more complicated and a proper formulation of the inverse problem shows that one needs to recover the values of a number of parameters along with the scattering potential. The short exposition here closely follows the one given in [5].

First, there are parameters that have no corresponding interpretation in the actual real-world ET experiment. The optical setup used in deriving the forward operator does not correspond to the actual setup in the TEM and some of the parameters defining this setup enters into the definition of $PSF^{re}$ and $PSF^{im}$. Formally, different choices of these parameters can define the an optical setup that has the same imaging properties as the actual setup in the TEM. However, there is a natural way to choose these parameters prior to reconstruction and therefore we considered them as known to sufficient degree of accuracy. Next, there are parameters, such as detector related parameters (e.g. $\text{gain}_{i,j}$ and the parameters that enters into $PSF_{det}$), that can be determined by separate calibration experiments independently of the ET data collection. These are also considered as known prior to reconstruction.

A more difficult class of parameters are those that are independent of the specimen but unique for each ET data collection. Some of these, such as the wavenumber k and magnification M, are in most cases known to sufficient degree of accuracy. However, the defocus $\Delta z$, spherical aberration $C_s$, and some of the envelope parameters have nominal values that must be adjusted, either by an analysis of the recorded micrographs and/or by performing additional measurements after the ET the data collection. The problem of determining these parameters is usually referred to as CTF estimation.

Finally, there are parameters that depend on the specimen. There are two examples of such parameters. The first relates to the fact that in ET one is dealing with a region of interest problem (local tomography), so one has a predefined region of interest (ROI) $\Omega \subset \mathbb{R}^3$ and one seeks f in a predefined region of interest (ROI) $\Omega \subset \mathbb{R}^3$ which is a strict subset of the support of f. Since $\Omega$ is subset of the support of f, when reconstructing f one would have to make assumptions regarding the values of f outside the $\Omega$. A typical such assumption is that f equals some constant average value outside $\Omega$ which then becomes a specimen dependent parameter. More formally, define $f_{local}:f|_\Omega$ and set $\Delta l(\omega, \chi)$ to denote the path length of the part of the line $t \mapsto t\omega + \chi$ that lies outside the region of interest (ROI) $\Omega$, but inside the support of f. Let the constant $\gamma^{re} + i\gamma^{im} \in \mathbb{C}$ represent the average value of f outside the ROI, so in (19) we need to introduce the following approximation:

$$P(f^{re})(\omega, \chi) \approx P(f_{local}^{re})(\omega, \chi) + \gamma^{re} \Delta l(\omega, \chi)$$

$$P(f^{im})(\omega, \chi) \approx P(f_{local}^{im})(\omega, \chi) + \gamma^{im} \Delta l(\omega, \chi).$$

Note that equality holds when the line is entirely in $\Omega$. The $\gamma^{re}$ and $\gamma^{im}$ parameters are our specimen dependent parameters. The other example of a specimen dependent parameter is when one assumes that the imaginary part of the scattering potential is proportional to the real part. More formally, assume that $$f(\chi) = (Q_{ph} + iQ_{amp})F(\chi) \quad (23)$$

for constants $Q_{ph}, Q_{amp} > 0$ and some function $F: \mathbb{R}^3 \to \mathbb{R}^+$. The ratio $Q_{amp}/Q_{ph}$ is called the amplitude contrast ratio. Under this assumption, the intensity generated by a single electron becomes $$I(f)(\omega, z) = \frac{1}{M^2}\left(1 - \left[\{PSF(\omega, \cdot) \underset{\omega^\perp}{\circledast} \mathcal{P}(F)(\omega, \cdot)\}\left(\frac{z}{M}\right)\right]k^{-1}\right)$$

which in turn yields the following expression for the forward operator:

$$\mathcal{T}(F)(\omega)_{i,j} = \frac{\text{gain}_{i,j}|\Delta_{i,j}|\text{Dose}(\omega)}{M^2}\left(\left\{PSF_{det}\underset{\omega^\perp}{\otimes}1\right\}(z_{i,j}) - \left\{PSF_{det}\underset{\omega^\perp}{\otimes}\left[\left\{PSF(\omega,\cdot)\underset{\omega^\perp}{\otimes}\mathcal{P}(F)(\omega,\cdot)\right\}\left(\frac{\cdot}{M}\right)\right]\right\}(z_{i,j})k^{-1}\right) + \varepsilon_{i,j}.$$

The point spread function PSF depends on $Q_{amp}$ and $Q_{ph}$ and is given as $$PSF(\omega,z) := \{Q_{ph}PSF^{re}(\omega,\cdot)\underset{\omega^\perp}{\otimes}1 + Q_{amp}PSF^{im}(\omega,\cdot)\}(z).$$

With this assumption one needs to recover the scaling factor (amplitude contrast ratio), which is specimen dependent.

The true inverse problem for ET is a multicomponent inverse problem where we have to recover not only the scattering potential f but also a number of parameters. The space $\mathcal{X}$ of unknowns in the inverse problem in ET therefore naturally splits in the following way:

$$\mathcal{X} = \mathcal{V} \times Z.$$

Here, $\mathcal{V} \subset \mathscr{L}^1(\Omega,\mathbb{C})$ is the set of complex valued functions that have positive real and imaginary parts and in ET we require that $\mathcal{V} \subset \mathscr{L}^1(\Omega,\mathbb{C}) \cap \mathscr{L}^2(\Omega,\mathbb{C})$. If one assumes that (23) holds at the expense of introducing the amplitude contrast ratio as an unknown parameter, then $\mathcal{V}$ is the set of positive real valued functions. Z is a finite dimensional vector space whose elements are the various parameters that are considered unknown prior to reconstruction.

Example

Finally we show an example of how the of the invention on the inverse problem in ET. We create ET data using a simulator based on (21) with the forward operator in (22). The phantom, i.e. the object to be reconstructed, is the RNA polymerase II, and actual scattering potential is calculated from the protein data base information of the RNA polymerase II. The size of the RNA polymerase II is about 400 kDa and it is assumed to be embedded in an amorphous ice slab that is 50 nm thick. The simulator allows generation of images similar to those recorded in an electron microscope. In the simulator tests, an underfocus of 1 μm was used and a full single axis tilt series was produced comprising 121 tilts between −60° and 60°.

The three-dimensional reconstruction from the present innovation is compared both to the original phantom (i.e. the true answer) and to the filtered backprojection reconstruction (FBP) that has been regularized by an additional low-pass filtering (low-pass FBP). This latter filtering, which in our case reduces the resolution to 7 nm, is necessary in order to gain stability and the above value for the low-pass filtering represents the best trade off between stability and resolution if FBP is to be used on this particular example.

Figure 4:
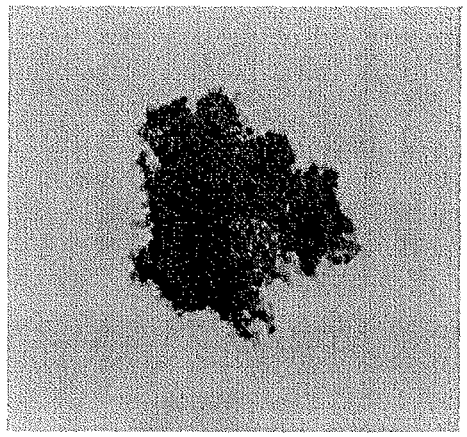
FIGS. 4-5 illustrates image result from the method illustrated in FIG. 1 compared to known technology.
Figure 4:
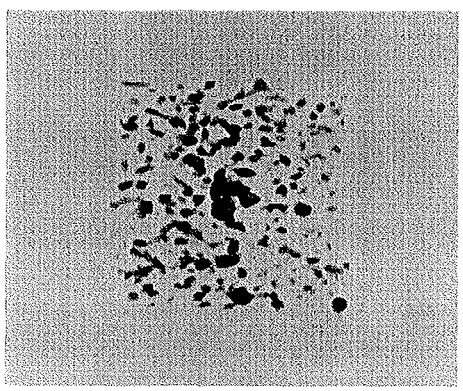
Figure 4:
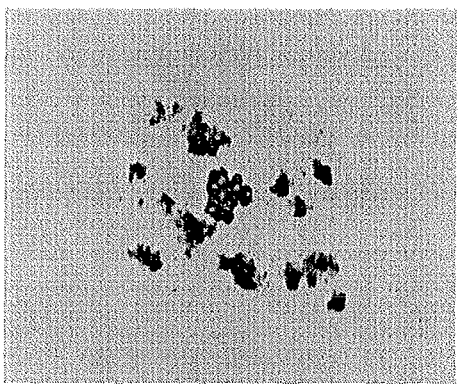

FIG. 4 shows volume rendered views of the three-dimensional reconstruction from simulated ET data of the RNA polymerase II as described above. In FIG. 4a the true phantom is shown. FIG. 4b shows a reconstruction using low-pass FBP and 4c shows a reconstruction using the present invention and they are contoured individually to optimize image quality.

Figure 5:
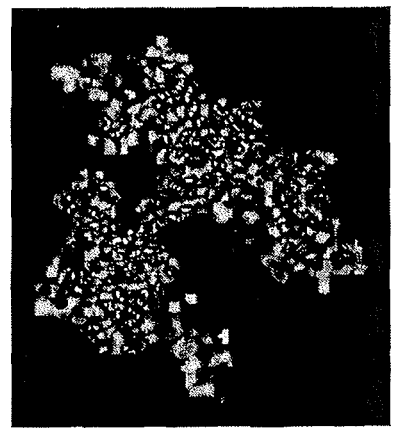
Figure 5:
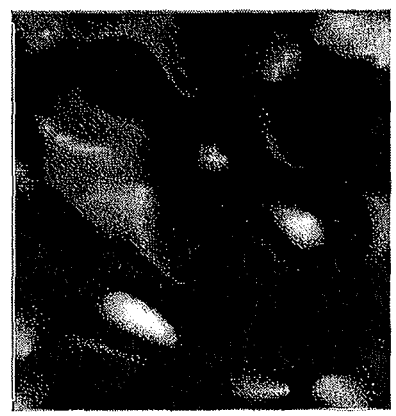
Figure 5:

FIG. 5 shows a tomogram (i.e. slice) through the three-dimensional reconstruction from simulated ET data of the RNA polymerase II as described above. No contouring or other types of image processing is applied. FIG. 5a shows a true phantom, FIG. 5b a low-pass filtered FBP reconstruction, and FIG. 5c the reconstruction using the present invention.

We see clearly that the present invention, as compared to the FBP approach, produces reconstructions with higher resolution and where the background clutter is severely suppressed.

REFERENCES

[1] A. B. Bakushinsky and M. Yu. Kokurin. *Iterative Methods for Approximate Solution of Inverse Problems*. Number 577 in Mathematics and Its Applications. Springer Verlag, 2004.
[2] A. Cimetiére, F. Delvare, M. Jaoua, and F. Pons. Solution of the Cauchy problem using iterated Tikhonov regularization. *Inverse Problems*, 17:553-570, 2001.
[3] H. W. Engl, M. Hanke, and A. Neubauer. *Regularization of inverse problems*, volume 375 of *Mathematics and its Appliations*. Springer Verlag, 2000.
[4] H. W. Engl and P. Kügler. Nonlinear inverse problems: theoretical aspects and some industrial applications. In V. Capasso and J. Périaux, editors, *Multidisciplinary Methods for Analysis, Optimization and Control of Complex System*, number 6 in Mathematics in Industry. The European Consortium for Mathematics in Industry, pages 3-48. Springer Verlag, 2005.
[5] D. Fanelli and Ö. Öktem. Electron tomography: A short overview with an emphasis on the absorption potential model for the forward problem. Submitted to Inverse Problems, 2007.
[6] J. Frank. *Three-dimensional electron microscopy of macromolecular assemblies*. Oxford University Press, 2nd edition, 2006.
[7] G. Golub and V. Pereyra. Separable nonlinear least squares—the variable projection method and its applications. *Inverse Problems*, 19:1-26, 2003.
[8] D. Gourion and D. Noll. The inverse problem of emission tomography. *Inverse Problems*, 18:1435-1460, 2002.
[9] M. Hanke and C. W. Groetsch. Nonstationary iterated Tikhonov regularization. *Journal of Optimization Theory and Applications*, 98(1):37-53, 1998.
[10] P. W. Hawkes and E. Rasper. *Principles of Electron Optics*. Volume 3. *Wave Optics*. Academic Press, 1994.
[11] M. A. Hayat. *Principles and techniques of electron microscopy*. Cambridge University Press, 4:th edition, 2000.
[12] Q.-N. Jin and Z.-Y. Hou. On the choice of the regularization parameter for ordinary and iterated Tikhonov regularization of nonlinear ill-posed problems. *Inverse Problems*, 13:815-827, 1997.
[13] S. Masich, T. Östberg, L. Norlén, O Shupliakov, and B. Daneholt. A procedure to deposit fiducial markers on vitreous cryo-sections for cellular tomography. *Journal of Structural Biology*, 2006. Accepted and available online.
[14] E. Resmerita. Regularization of ill-posed problems in Banach spaces: convergence rates. *Inverse Problems*, 21:1303-1314, 2005.
[15] H. Rullgård, O. Öktem, and U. Skoglund. A componentwise iterated relative entropy regularization method with updated prior and regularization parameter. *Inverse Problems*, 23:2121-2139, 2007.

The invention claimed is:
1. A method for providing reliable solutions to multicomponent inverse problems comprising the steps of:
   carrying out each of the following steps in a processing unit of a computer;

given a multicomponent inverse problem, determining reliable prior knowledge about its solution, determining an initial guess for a solution, and determining a corresponding forward operator;

given measured data, deciding upon a model for the stochasticity of the data;

deciding upon which component-wise reconstruction/regularization method to use for recovering each component separately based on said prior knowledge of the solution, said model for the stochasticity of the data, and said forward operator;

deciding upon an updating scheme for the component-wise prior knowledge of the solution based on said component-wise reconstruction/regularization method;

deciding upon a component-wise updating scheme for parameters of said component-wise regularization/reconstruction method based on said model for the stochasticity of the data, said pre-processed data, and said updated component-wise prior knowledge of the solution; and producing a sequence which is obtained by intertwining two sequences, the first of the sequences from an iterated reconstruction/regularization method and the second of the sequences from a component-wise reconstruction/regularization method using said reconstruction/regularization method for each component separately and applying said updating schemes for the component-wise prior knowledge of the solution and reconstruction/regularization parameters.

2. The method according to claim 1, wherein said prior updating within the sequence is combined with a smoothing operation.

3. The method according to claim 1, wherein a variational regularization method is used in the said component-wise reconstruction/regularization for a specific component.

4. The method according to claim 3, wherein a tolerance based variational regularization method is used as said variational regularization method and said updating of the corresponding regularization parameter (which is the tolerance level) is made without prior knowledge of the total error in the data.

5. The method according to claim 4, wherein the constrained optimization problem defining the regularization method is not fully solved.

6. The method according to claim 4, wherein the constrained optimization problem defining the regularization method is solved only in a low-dimensional subspace of the space containing the component.

7. The method according to claim 3, wherein the relative entropy is used as a regularizing functional.

8. The method according to claim 3, wherein the covariance weighted least squares norm is used as data discrepancy functional.

9. The method according to claim 1, wherein a non-linear least squares reconstruction is used in the said component-wise reconstruction/regularization for a specific component.

10. A data acquisition device comprising the processing unit, a non-transient computer readable memory unit, and an interface unit, wherein the processing unit is arranged to run the reconstruction method according to claim 1 stored in the memory unit using data obtained using the interface unit.

11. A computational device with a non-transient computer readable memory medium comprising data representing a solution of the inverse problem obtained from the method according to claim 1.

* * * * *

UNITED STATES PATENT AND TRADEMARK OFFICE
CERTIFICATE OF CORRECTION

PATENT NO.       : 8,468,189 B2                                                             Page 1 of 1
APPLICATION NO. : 12/513943
DATED            : June 18, 2013
INVENTOR(S)      : Öktem et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1077 days.

Signed and Sealed this
Eighth Day of September, 2015

Michelle K. Lee
*Director of the United States Patent and Trademark Office*